US006482309B1

(12) United States Patent
Green et al.

(10) Patent No.: US 6,482,309 B1
(45) Date of Patent: Nov. 19, 2002

(54) ELECTROLYTIC GENERATION OF NASCENT IODINE AS A METHOD OF TREATMENT AND FOR THE PREVENTION OF INFECTIONS ASSOCIATED WITH MEDICAL IMPLANT DEVICES

(75) Inventors: Terrence R. Green, Lake Oswego, OR (US); Jack H. Fellman, McMinnville, OR (US)

(73) Assignee: OxiBio, Inc., Portland, OR (US)

( * ) Notice: Subject to any disclaimer, the term of this patent is extended or adjusted under 35 U.S.C. 154(b) by 0 days.

(21) Appl. No.: 09/694,110

(22) Filed: Oct. 19, 2000

Related U.S. Application Data

(60) Provisional application No. 60/160,555, filed on Oct. 20, 1999.

(51) Int. Cl.[7] ................................................. C25B 1/24

(52) U.S. Cl. ........................ 205/619; 205/701; 204/242; 204/260; 204/272

(58) Field of Search ................................. 205/619, 701; 204/242, 260, 272

(56) References Cited

U.S. PATENT DOCUMENTS

| | | | | |
|---|---|---|---|---|
| 2,355,231 | A | * 8/1944 | Moore | 205/701 |
| 4,278,548 | A | 7/1981 | Bettinger et al. | 210/636 |
| 4,312,833 | A | 1/1982 | Clough et al. | 422/30 |
| 4,411,648 | A | 10/1983 | Davis et al. | 604/21 |
| 4,476,108 | A | 10/1984 | Kessler et al. | 424/50 |
| 4,583,548 | A | 4/1986 | Schmid | 128/639 |
| 5,156,164 | A | 10/1992 | LeVeen et al. | 128/832 |
| 5,230,783 | A | 7/1993 | Scortichini et al. | 204/153.12 |
| 5,246,561 | A | 9/1993 | Scortichini et al. | 204/415 |
| 5,419,816 | A | * 5/1995 | Sampson et al. | 205/556 |
| 5,607,681 | A | 3/1997 | Galley et al. | 424/405 |

(List continued on next page.)

FOREIGN PATENT DOCUMENTS

| | | |
|---|---|---|
| EP | 0 346 058 A1 | 12/1989 |
| EP | 0 578 612 A1 | 1/1994 |

OTHER PUBLICATIONS

A. Shikani, et al., "Polymer–Iodine Inactivation of the Human Immunodeficiency Virus", Journal of the American College of Surgeons, Sep. 1996, vol. 183, pp. 195–200.

(List continued on next page.)

*Primary Examiner*—Arun S. Phasge
(74) *Attorney, Agent, or Firm*—Heller Ehrman White & McAuliffe LLP

(57) ABSTRACT

An anti-infective device generally comprising an oxidant generating formulation contained within at least a section of the device configured to electrolytically generate an anti-infective oxidant. The device has at least one of a cathode member and an anode member in the section of the device, configured to electrolyze the oxidant generating formulation to electrolytically generate the anti-infective oxidant. A power source is electrically connected to the cathode and anode members such that current passes between the cathode and anode members. In one embodiment, the oxidant generating formulation comprises a solid dispersed in a polymeric wall of the device. In a presently preferred embodiment, the cathode and anode members are completely embedded within the polymeric wall of the device, although in some embodiments they may be partially embedded within the polymeric wall of the device. In another embodiment, the oxidant generating formulation comprises a solution contained within a chamber in the device. The cathode and anode members are located within the chamber in contact with the solution. The electrolytically generated anti-infective substance is preferably elemental iodine. In one embodiment, the oxidant generating formulation comprises an iodide, which is oxidized at the anode member. In another embodiment, the oxidant generating formulation comprises an iodate which is reduced at the cathode member. Preferably, a proton donor is also present in the iodate containing oxidant generating formulation.

25 Claims, 6 Drawing Sheets

U.S. PATENT DOCUMENTS

| | | | | |
|---|---|---|---|---|
| 5,609,742 A | | 3/1997 | Sampson et al. | 204/536 |
| 5,695,458 A | | 12/1997 | Shikani et al. | 604/4 |
| 5,705,050 A | * | 1/1998 | Sampson et al. | 205/687 |
| 5,762,638 A | | 6/1998 | Shikani et al. | 604/265 |
| 5,849,291 A | | 12/1998 | Kessler | 424/94.4 |

OTHER PUBLICATIONS

Kristinsson KG, "Antimicrobial Activity Of Polymers Coated With Iodine–Complexed Polyvinylpyrrolidone", J Biomater Appl, 1991 Jan; 5(3): 173–84.

M. Tyagi, et al, "Preparation and Antibacterial Evaluation of Urinary Balloon Catherer", ISA, 1997, Paper #97–040, pp. 240–245, no month.

W. Morain, et al, "Iodinated Silicone–An Antibacterial Alloplastic Material", Plastic & Reconstructive Surgery, Feb. 1977, vol. 59—No. 2, pp. 216–222.

L. Birnbaum, et al, "The Role of Iodine–Releasing Silicon Implants In Prevention Of Spherical Contractures In Mice", Plastics & Reconstructive Surgery, Jun. 1982, vol. 69, No. 6, pp. 956–959.

D.G. Maclellan, "Foreward", Dermantology 1997, suppl 2): 1–2, http://BioMedNet/karger, no month.

E. T. Houang, et al, "Absence Of Bacterial Resistance To Providone Iodine", Journal of Clinical Pathology, 1976, vol. 29, pp. 752–755, no month.

P. Caufield, et al, "In Vitro Susceptibility Of Streptococcus Mutans 6715 To Iodine And Sodium Fluoride, Singly And In Combination, At Various pH Values", Antimicrobial Agents And Chemotherapy, Jul. 1982, pp. 115–119.

B. Jansen, et al, "In–Vitro Efficacy Of A Central Venous Catheter Complexed With Iodine To Prevent Bacterial Colonization", Journal of Antimicrobial Chemotheraphy (1992) 30, pp. 135–139, no month.

Philip J. Scarpace, et al, "Preparation and Immunological Characteristics of Biologically Active Radioiodinated Human Calcitonin", Endocrinology 101 (1977) pp. 1398–1405, no month.

A.G. Teulings, et al., "Study of Electrolytic Labeling Of Fibrinogen With Iodine By Sephadex G–ro Gel Filtration", Clin. Chim. Acta. 27 (1970) pp. 57–64, no month.

K. Krohn, et al, "Studies of Radioiodinated Fibrinogen", Biochimica Biophysica. Acta, 285 (1972) pp. 404–413, no month.

A. Massaglia, et al, "Iodination Of Insulin In Aqueous And Organic Solvents", Biochemistry Journal (1969) 115–11, no month.

S.T. Nielsen, et al., "The Electrolytic Preparation Of Bioactive Radioiodinated Parathyroid Hormone of High Specific Activity", Analytical Biochemistry 92, 67–73 (1979), no month.

E. Barabas, et al., "Povidone Iodine", Analytical Profiles of Drug Substances and Excipients, vol. 25, pp. 341–462, (no date).

P.G. Malan, et al, "An Electrolytic Procedure For Iodination Of Glycoprotein And Protein Hormones", Proceedings of the Society of Endocrinology, pp. XII, (no date).

H. H. LeVeen, et al., "The Mythology of Povidone–Iodine And The Development of Self–Sterilizing Plastics", Surgery, Gynecology & Obstetrics, Feb. 1993, vol. 176, pp. 183–190.

X. Zhang, et al., "Antiinfective Coatings For Indwelling Medical Devices", Medical Plastics and Biomaterials, Nov./Dec. 1997.

K. Gupta, et al., "Increasing Prevalence of Antimicrobial Resistance Among Uropathogens Causing Acute Uncomplicated Cystitis in Women", JAMA, Feb. 24, 1999, vol. 281, No. 8.

* cited by examiner

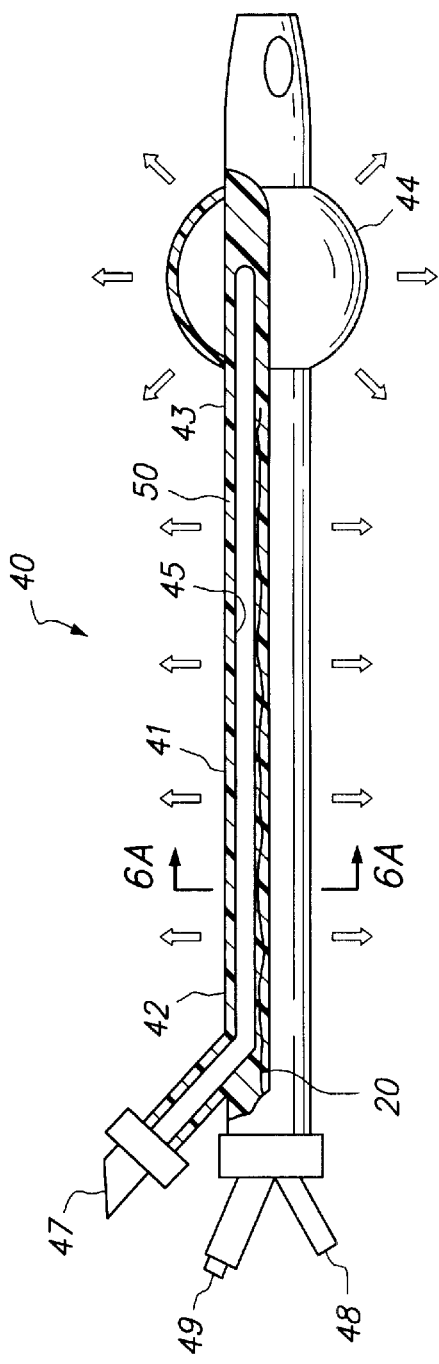
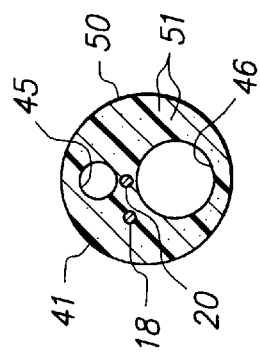
FIG. 6
FIG. 6A

US 6,482,309 B1

ELECTROLYTIC GENERATION OF NASCENT IODINE AS A METHOD OF TREATMENT AND FOR THE PREVENTION OF INFECTIONS ASSOCIATED WITH MEDICAL IMPLANT DEVICES

CROSS REFERENCE TO RELATED APPLICATIONS

This application claims the benefit under 35 USC 11 9(e) of copending Provisional Application No. 60/160,555, filed on Oct. 20, 1999. This application and other documents referred to elsewhere in the specification of this application are incorporated herein by reference in their entireties.

FIELD OF THE INVENTION

The present invention relates to compositions and devices for transferring anti-infective activity to medical devices through electrolytic generation of elemental iodine, allowing for its transfer to the polymer base of urinary and venous catheters, wound drain tubes, and other medical devices, conferring to such devices prophylactic and therapeutic treatment of implant-linked infections.

BACKGROUND OF THE INVENTION

Introduction of medical devices implanted into the body can lead to serious nosocomial infections. Implanted medical devices (e.g., venous and arterial catheters, neurological prostheses, wound drains, urinary "Foley" catheters, peritoneal catheters, and other lumenal indwelling devices), while sterilized and carefully packaged to guard against introduction of pathogens during implantation, pose a risk during insertion, and subsequently. During insertion bacteria can be picked up from the skin and carried into the insertion site where bacterial colonization may ensue. In the case of urinary and venous catheters, especially those used long term, there is a significant threat of microbial growth along the exterior surface of the catheter. This can lead to chronic urinary tract infections (CUTI), or septicemia in the case of venous and arterial catheters, thrombolytic emboli caused with infections introduced by the catheter, and other life-threatening complications, especially among the elderly. In cerebrospinal fluid shunt catheters the incidence of infections is unacceptably high, especially in neonates, varying from 2 to 31% depending upon the age group and hospital setting in which the surgery is conducted.

Methods aimed at circumventing this problem have included irrigating the implant site with antibiotic, applying various antibiotic ointments or antibiotic impregnated sponges near the exterior opening by which infection most likely occurs, impregnating the polymer base coating the implant device with antibiotics, or silver, either as a heavy metal or in combination with antibiotics, or treatment of patients systemically with antibiotics. Despite the foregoing attempts at preventing infections, these methods of preventing and treating infections have not proven satisfactory. There remains a need in the art to mitigate the risk of infection from such devices.

It is known, for example, that the long term uses, and misuse, of antibiotics often results in the selection of antibiotic resistant strains. Hence, in general, systemic antibiotic therapy is ill advised and ineffective in warding off CUTI, for example. The secondary side effects of systemic antibiotic treatments can also pose a serious risk to many patients. Furthermore, in many implant sites, the formation of fibrous tissue around the implant site reduces the supply of blood to the implant cavity thereby precluding systemic antibiotic treatment of the critical space between the implant and capsular endothelial wall. In the case of a urinary catheter (e.g., Foley catheter), antibiotics injected as a coating in the urinary canal may be washed out during drainage through leakage of some urine along the urinary tract outside the catheter, or resorbed before they can achieve sufficient levels to effectively kill bacteria growing within localized regions of the urinary tract.

It can thus be appreciated that there is a pressing need for the development of better methods of preventing and treating infections caused with the implantation of medical devices into body cavities, particularly for the development of methods and devices which circumvent the problem of selecting out antibiotic resistant organisms. The problem is particularly acute since it is known that when catheters, and other indwelling lumenal devices, are inserted into body cavities such as the urinary tract, venous or arterial vessels, or into wound or surgical sites, a biofilm forms rapidly on the walls of the implant device. Bacteria then propagate free from attack by the body's own phagocytic defense system, and also free from systemic antibiotic treatments (Gristina, A.G., Science 237: 1588–1595 (1987); Zhang, X. et al., Medical Plastics and Biomaterials, Nov. 1997, pp. 16–24).

Free elemental iodine is attractive as an anti-infective agent. There are no known organisms which have developed resistance against its oxidizing activity in attacking critical sulfhydryl groups, and other functional groups in proteins, essential for bacterial survival (Second Asian Pacific Congress on Antisepsis in Postgrad. Med. J. 69 (suppl. 3), 1993: S1–S134; Third Asian Pacific Congress on Antisepsis in Dermatology 195 (suppl. 2), 1997: S1–S120). A few parts per million (ppm) in solution is sufficient to kill bacteria and viruses (LeVeen et al. (1993) Gynecology & Obstetrics 176: 183–190; Barabas, E. S. and Brittain, H. G. (1998) in Analytical Profiles of Drug Substances and Excipients (ed., Brittain, H. G.) Vol. 25, AP, San Diego, pp. 341–462). On the other hand, because of its high degree of diffusion through water, air and lipids, and its reactivity as an oxidizing agent, elemental iodine is difficult to handle in a clinical setting.

Methods of stabilizing iodine in solution illustrated by the formulation, Povidone-iodine, for example, are well known to those in the art. This formulation has been tried without satisfactory success in conferring to catheters anti-infective properties. Povidone-iodine washes free of devices as a coating of insufficient duration to significantly reduce the incidence of infections brought on following implantation, particularly in complex biological media. Jansen et al. (J. Antimicrobial Chemotherapy 30: 135–139 (1992)), and Kristinsson et al. (J. Biomaterials Applications 5: 173–184 (1991)), sought to confer to catheters anti-infective activity by preloading the lumen with iodine complexed with polyvinylpyrrolidone (PVP). While they were able to demonstrate weak anti-infective activity in aqueous buffered solutions, this strategy proved unsatisfactory in complex media. Jansen reported that the activity conferred by this technique lasted for less than 3 hours in serum.

Povidone-iodine as it is commercially formulated with a total iodine content of 10,000 ppm also introduces a high iodine exposure level to the patient of which only about 1 ppm is free iodine, the form necessary to affect microbial killing. PVP, the binding agent used in trapping iodine in aqueous solutions in a bound form, is also problematic in retarding wound-healing (LeVeen et al. (1993) Gynecology & Obstetrics 176: 183–190). The short-lived retention of Povidone-iodine coatings on implant devices, the fact that binding agents such as PVP aggravate wound-healing, and the fact that the free form of iodine in Povidone-iodine at 1 ppm is below the essential ~2 ppm level of free iodine required for efficient microbial killing, points out the need for a better method of presenting iodine as an anti-infective agent to catheters, and other indwelling implant devices (e.g., wound drains).

Morain and Vistnes (Plastic & Reconstructive Surgery 59: 216–222 (1977)) sought to impregnate silicone discs with elemental iodine by soaking discs in 95% ethanolic solutions in which crystalline iodine had been dissolved, and then tested the discs for anti-infective activity. While they were able to demonstrate the release of anti-infective activity in their iodine impregnated disc samples, they concluded that the use of iodine was "contraindicated" because of concern that it would add to the vinyl group of polymethylvinylsiloxane in the formulations they used, potentially altering "the substance sufficiently that an entirely new set of physiochemical properties might result." It is also apparent that the method of impregnating an implant using crystalline iodine and an alcoholic solution is impractical in a clinical setting. Iodine crystals in combination with alcohol can cause severe chemical burns if put into direct contact with tissues, it is difficult to control dosing of crystalline iodine in a reliable fashion, and messy working with mixtures of crystalline iodine and alcohol. Thus the practical obstacles of preparing impregnated anti-infective implants using this technology pose serious logistical problems in the handling and release of iodine.

Birnbaum et al. (Plastic & Reconstructive Surgery 69: 956–959 (1982)) sought to confer to silicone breast implants anti-infective activity by injecting Povidone-iodine solutions into the internal cavity of the implants in studying prevention of spherical contractures believed to be caused by inflammation, but found comparable fibrosis, collagen deposition and inflammation to that of control animals implanted with silicone implants lacking anti-infective activity. Birbau et al. taught that in their formulation "the effects of iodine are limited to a proscribed period of time, following which all inhibitory activity is lost." They concluded that ". . . Bacteria arriving subsequent to this period of activity would not be inhibited. Fibrosis and late scar contracture might then ensue. . ." thus teaching away from the use of delivering free iodine into silicone polymer implants.

LeVeen and LeVeen (U.S. Pat. No. 5,156,164) claimed to have conferred bactericidal activity to a contraceptive sponge by impregnating the polyurethane polymer base comprising the sponge with an aqueous solution of free iodine made up in Lugol's solution. More recently, Shikani and Domb (U.S. Pat. No. 5,695,458; 5762638) described the fabrication of iodine impregnated polymer coatings of varying thickness prepared by dissolving elemental iodine into organic solvents which also contained organic polymers which were then layered and coated by dipping and drying steps over medical devices including blood handling collection bags, tubes, catheters, and the like. This technology involves multiple layering of iodine impregnated polymers, the spacing of additional layers of polymer lacking iodine dissolved in the organic solvents, and varying such steps aimed at retarding and managing the egress rates of free iodine from the polymer base to provide for a controlled anti-infective activity. Tyagi and Singh (Biomedical Sciences Instrumentation 33: 240–45 (1997)) in a similar fashion sought to confer to latex Foley urinary balloon catheters anti-infective activity by dipping the outer external surfaces of the latex balloon in toluene solutions comprising a mixture of elemental iodine and latex, and then drying and storing catheters treated in this manner at low temperature in polythene bags prior to use. Neither the polyrurethane nor latex methods are amenable to on site delivery of anti-infective activity to an existing catheter or implant device at the bedside, or in the surgical suite. The use of organic solvents, drying times and multiple dipping steps make these methods impractical in a clinical setting in conferring anti-infective activity to the implant device.

The latter techniques of entrapping elemental iodine within a polymer base as taught by A LeVeen and LeVeen, Shikani and Domb, and Tyagi and Singh, rely, in general, on starting with free elemental iodine dissolved within a solvent system, and trapping it within a polymer base, a process wrought with technical difficulties. The layering and drying steps used in the art taught by Shikani and Domb, and Tyagi and Singh, moreover, are costly and time consuming. In addition, none of the methods starting with free elemental iodine address the problem of how to ensure a long shelf life for iodine entrapped within the polymer base of the implant device. Once the device is fabricated and loaded with iodine, it can be appreciated by those knowledgeable in the art that iodine will begin to diffuse into the air because of the inherent chemical properties of iodine to disperse free of its initial site of deposition. Furthermore, the high degree of reactivity of free iodine is a drawback to these methods. It can be anticipated, for example, that iodine will react and become depleted from the device in encountering varying reducing compounds coming into contact with the device. Such compounds capable of depleting the iodine entrapped within the device may be in the form of gases, liquids or solids including the wrapping materials in which the devices are stored. In addition to these limitations, in the art taught by Shikani and Domb, and Tyagi and Singh, the layering of varying polymer layers atop one another using organic solvents in which iodine is dissolved is limited to polymers which are compatible with one another in forming strong and uniform adhesive bonds, and which will not swell or alter shape when wetted and presented to a biological site of treatment. This is contrary to the properties of many medical grade polymers used in medical devices that have a tendency to swell and distort in shape once placed within the body. Polymer swelling and distortion is unacceptable in the art taught by Shikani and Domb since the latter phenomenon results in rupturing of the adhesive bonds between the iodine coated layers of the implant device and loss of control in the release rates of free iodine egressing from the device.

An alternate method of conferring to medical devices anti-infective activity embodied in the present invention involves electrolytic generation of nascent iodine at the site requiring anti-infective treatment. In one embodiment of the invention, an anodic wire lead serves upon application of a low level of current generated from a 1.5 volt battery connecting to the anode, and a cathodic wire lead also inserted in parallel with the anodic lead, to oxidize inorganic iodide, resulting in the formation of nascent iodine, and conferring to the implant anti-infective properties. In an alternate form of this invention, oxide salts of iodine, dispersed in solution, or within the polymer base of the implant device, are reduced at the cathodic lead wire also placed in the iodine oxide mixture in close proximity to a parallel anodic wire lead.

SUMMARY OF THE INVENTION

This invention is directed to an anti-infective device generally comprising an oxidant generating formulation contained within at least a section of the device configured to electrolytically generate an anti-infective oxidant. The device has at least one of a cathode member and an anode member in the section of the device, configured to electrolyze the oxidant generating formulation to electrolytically generate the anti-infective oxidant. A power source is electrically connected to the cathode and anode members such that current passes between the cathode and anode members. Electrical conductors may be provided which electrically connect the cathode and anode members to the power source.

In one embodiment, the oxidant generating formulation comprises a solid dispersed in a polymeric wall of the device. In a presently preferred embodiment, the cathode and anode members are completely embedded within the polymeric wall of the device, although in some embodiments they may be partially embedded within the polymeric wall of the device. In another embodiment, the oxidant generating formulation comprises a solution contained within a chamber in the device. The cathode and anode members are located within the chamber in contact with the solution.

The device may comprise a medical device such as a catheter, drain tube, or implant. Alternatively, the device may comprise an insert member configured to be slidably insertable into a lumen of a medical device or insertable around the medical device, to transfer the anti-infective oxidant from the device into a wall of the medical device defining the medical device lumen.

In a presently preferred embodiment, the electrolytically generated anti-infective substance is elemental iodine. In one embodiment, the oxidant generating formulation comprises an iodide, which is oxidized at the anode member. In another embodiment, the oxidant generating formulation comprises an iodate which is reduced at the cathode member. Preferably, a proton donor is also present in the iodate containing oxidant generating formulation.

This invention takes advantage of the chemical properties of iodine formed at the lead wires to diffluse freely to desired sites of the implant polymer base where anti-infective activity is needed to prophylactically prevent, and to treat, infections. By generating nascent iodine from precursor substrates, the invention allows for the fabrication of insert devices designed to be placed into existing implant devices, or, alternatively, direct incorporation of the invention into the design of an it implant device, conferring to the device anti-infective properties without the attendant problems of iodine instability and loss encountered in prior art. In addition, the invention has applications in treating devices applied topically where sterilization is important in preventing, or ameliorating, the spread of infections. Contact lenses, for example, must be cleansed regularly and sterilized to prevent introduction of infectious organisms to the eye during wearing of the lenses. Hence, the placement of lenses in a fabricated device having the aspects of the invention described herein can confer to the lens anti-infective properties, serving to sterilize and ameliorate the spread of infections to the eye from contaminated lenses. The invention described here is formulated using stable precursor substrates of nascent iodine, and thus it provides for reliable and long-term treatments in preventing, and eliminating, common infections associated with the implantation of medical devices into body cavities of patients.

The ability to exploit chemical formation of free iodine de novo, and positioning and transfer of elemental iodine using this invention for the treatment and prevention of infections, is of great advantage. It can be used on existing lumenal implant devices such as urinary, venous and arterial catheters, wound drains, and other indwelling lumenal devices, without the expense and retooling necessary in manufacturing anti-infective activity into devices already produced by manufacturers and in use clinically. Furthermore, this invention allows clinicians and users of this art to tailor the frequency of treatment to the needs of the patient in preventing, or treating, an infection, and thus this invention offers great flexibility in its application in the clinical setting.

BRIEF DESCRIPTION OF THE DRAWINGS

FIG. 6 illustrates a catheter, partially in longitudinal cross section, which embodies features of the invention.

FIG. 6A is a transverse cross sectional view of the catheter shown in FIG. 6, taken along line 6A–6A.

DETAILED DESCRIPTION OF THE INVENTION

Figure 1:
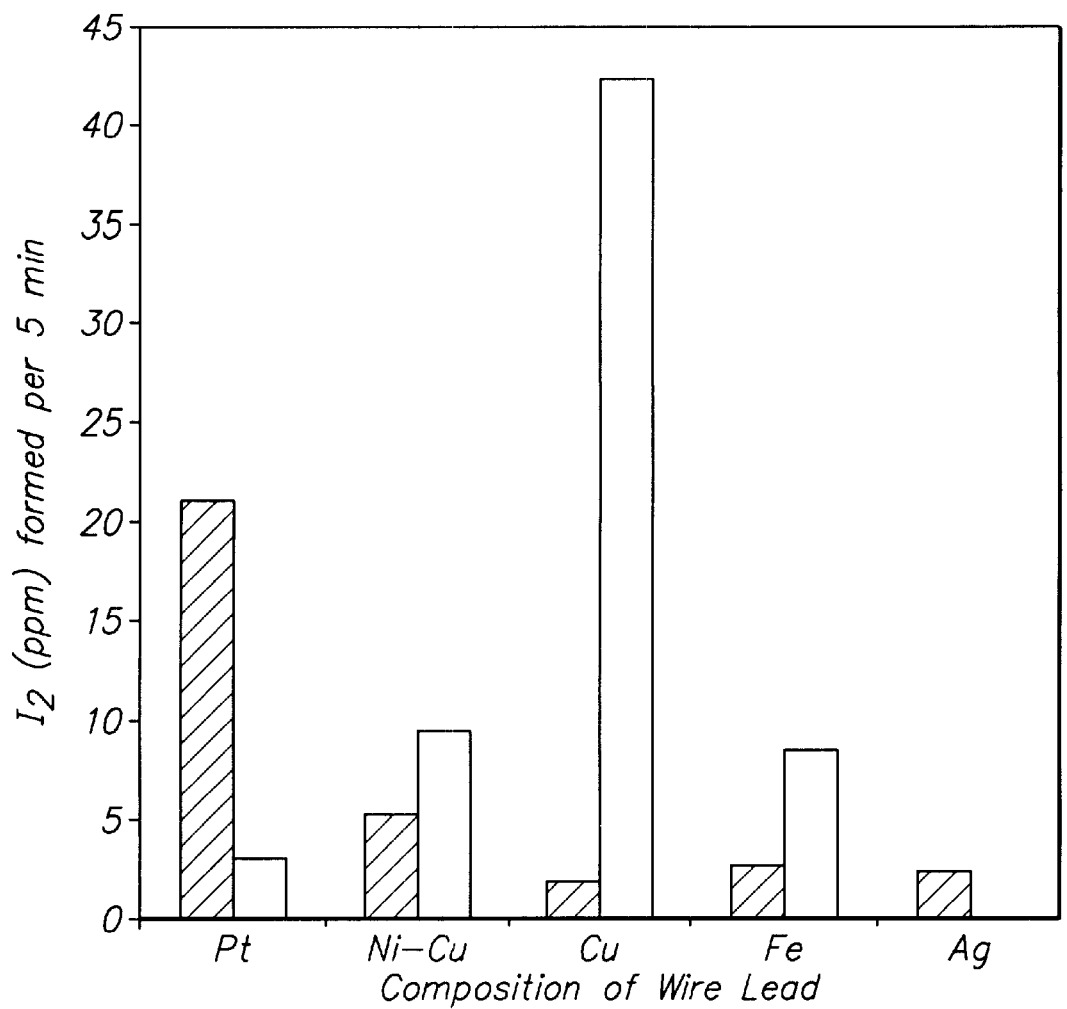
FIG. 1 compares rates of free nascent iodine formed after five minutes of electrolysis with immersion of varying metal wire leads (as indicated) in 5 ml solutions of potassium iodide (filled bars) versus corresponding rates in sodium iodate and citric acid solutions (hatched bars).

Overview of the Device and Formulation Chemistry

Varying methods and formulations for nascent iodine production to be used as an antiinfective have been described in prior art (U.S. Pat. Nos. 4,278,548, 4,312,833, 4,476,108, 5,232,914, 5,607,681, 5,648,075, 5,849,241). These methods have in common the presentation of inorganic iodide, an oxidant (either enzymatic or inorganic), a proton source and water as a solvating agent in combination to affect formation of free elemental iodine through oxidation and conversion of iodide into iodine in accordance with the following general equation:

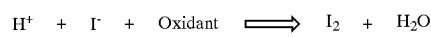

$$H^+ + I^- + \text{Oxidant} \rightleftharpoons I_2 + H_2O$$

Depending upon the oxidant used, other byproducts of the reaction may arise (vis., gluconate in the case of glucose oxidase wherein the proton generated in the formation of gluconic acid, and hydrogen peroxide formed with consumption of molecular oxygen, are converted to water concomitant with iodine formation). None of these methods involves the generation of nascent iodine by electrolytic means. Several examples of generating nascent iodine by electrical means have been described, however, for labeling proteins and various other substrates with radiolabeled iodine (U.S. Pat. Nos. 5,230,783, 5,2465,61; also see Krohn, K. et al. (1972) Biochim Biophys Acta 285 (2): 404–13; Malan, P. G. et al. (1974) J. Endocrinol. 61 (2): XLII; Massaglia, A. et al. (1969) Biochem. J. 115: 11–18; Nielsen, S. T. et al. (1979) Anal. Biochem. 92 (1): 67–73; Raad, I. et al. (1996) Biomaterials 17 (11): 1055–9; Pennisi, F. and Rosa, U. (1969) J. Nucl. Biol. Med. 13 (1): 64–70 ; Scarpace, P. J., and Deftos, L. J. (1977) Endocrinology 101 (5):1398–405; and Teulings, F. A. G., and Biggs, G. J. (1970) Clin. Chim. Acta 27: 57–64). There appears, however, to be no prior art describing methods, or fabrications of devices, for electrolytic generation of nascent iodine as an anti-infective agent.

In the present invention, the precise method of forming nascent elemental iodine starting with either inorganic iodide, or oxides of iodide, is not critical as long as nascent iodine is formed in sufficient quantity to permeate the walls of an implant device, or loading rod, whence its transfer to the surface walls of the implant device can ensue. Precursor substrates for formation of nascent iodine may be incorporated either in a solution encased in a suitable polymer base which will allow iodine to freely diffuse across its wall, or dispersed as solids within the polymer base making up the implant device. This precursor source for formation of nascent iodine may be referred to as a "precursor reservoir". Cathodic and anodic electrical lead wires must also be inserted into the precursor reservoir. These serve as the means of electrolytically oxidizing inorganic iodide in converting it to nascent iodine with passage of a low level of current through the lead wires, or in the case of oxides of iodine, electrolytically reducing the latter to nascent iodine.

Oxidation of inorganic iodide occurs at the anode. Reduction of oxides of iodine occurs at the cathode. Hence, positioning of the anodic, or cathodic, lead wire within the device designed to generate anti-infective activity is important. Depending upon the chemical composition of the id precursor reservoir (inorganic iodide v. oxides of iodine), the cathodic lead wire (in the case of oxides of iodine), or anodic lead wire (in the case of inorganic iodide), should be positioned in close proximity to the site where anti-infective nascent iodine formation is to be formed in the implant device. For example, for a precursor reservoir containing inorganic iodide the anodic lead wire should be placed preferably within the central core of the reservoir with the cathodic lead positioned more distal from the central core. In this design, nascent iodine will form centrally, and difffuse laterally in a more symmetrical pattern from the core of the implant, allowing for a more uniform dispersion of anti-infective activity to the peripheral surfaces of the implant. Conversely, where oxides of iodine make up the precursor reservoir, the cathodic lead wire should preferably be placed in the central core with the anodic lead wire located more peripheral to achieve the same effect as noted above.

The principle of electrolytically loading implant devices with anti-infective nascent iodine is based upon the propensity of free iodine to diffuse freely upon formation through the polymer base making up the implant device, and thus to disperse to the exterior walls of implant devices where anti-infective activity is needed in prophylactically preventing the establishment of an infection between the exterior walls of the implant device, and biofilms formed on the surface of the device. It is feasible to also cause the transfer of nascent iodine from one implant to a second implant device by causing nascent iodine to form in the first, and to then allow it to diffuise freely across the walls of the first implant into the walls of the second device. Hence, it is feasible to design an insert, or plug, fabricated out of a suitable polymer base, and containing the essential components required for electrolytic generation of nascent iodine.

Such devices may be designed in the shape of an elongated probe, rod or plug, as desired, to be placed into the lumenal cavity of an existing implant device such as a venous catheter, Foley urine catheter, wound drain tube, etc. By electrolytic generation of nascent iodine within the insert device, one can then effectively transfer iodine to the second implant. This embodiment of the invention allows one to use the invention in conferring to existing lumenal implant devices on the market anti-infective properties through transfer of nascent iodine to the latter implants. The power source for generating current can be a low voltage battery such as a 1.5 volt disposable battery. To achieve bacterial killing, the free iodine level egressing from the device should preferably attain a level of not less than 2 ppm nor exceed about 300 ppm within the body fluid to be treated as iodine egresses to the surface walls of the device receiving treatment.

Construction of the Implant Device

There are two embodiments of the anti-infective generating implant device. One is designed as an insert, plug, or reservoir, for transfer of anti-infective activity to an existing medical device. Wire leads and chemical formulations necessary for nascent formation of iodine are incorporated into the insert design. The other embodiment is as a stand-alone medical implant wherein the chemistry and electrical lead wires are incorporated into the polymer base of the implant, but where the form and function of the device is foremost. The inclusion of the electrolytic nascent iodine generating aspect in this latter embodiment is secondary, allowing for production of a self-contained implant device with "built-in" anti-infective activity by virtue of incorporating the electrolytic iodine generating system into the polymer base of the implant. Iodine generating activity is thus conferred to implant.

Figure 4:
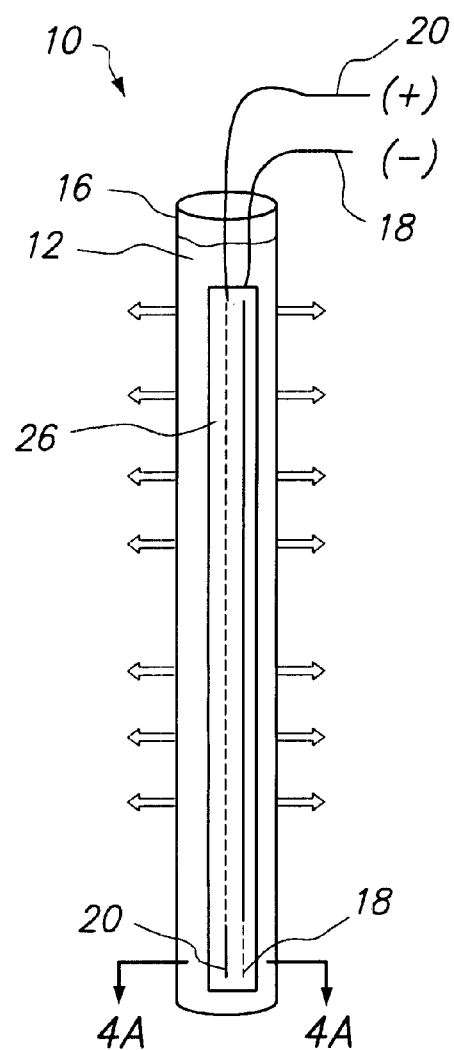
FIG. 4 illustrates a silicone fabricated insert member which embodies features of the invention, having a solution of an oxidant generating formulation contained within a chamber in the insert member.
Figure 4A:
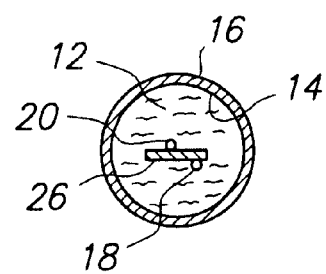
FIG. 4A is a transverse cross sectional view of the insert member shown in FIG. 4, taken along line 4A—4A.

FIG. 4 is a schematic drawing of a silicone fabricated insert member 10 which embodies features of the invention. The insert member comprises an oxidant generating formulation, such as an iodide or an iodate in a solution 12. The solution 12 is sealed inside a core or chamber 14 defined by a polymeric wall 16 of the insert member. A cathode member 18 and an anode member 20, generally comprising metal wires referred to as "lead wires", are located within the chamber 14. In the embodiment illustrated in FIG. 4, the entire length of each metal wire located in the solution is exposed to the solution 12, to thereby function as a cathode or anode, respectively. Alternatively, only a portion of the wires may be exposed, as for example where insulation is provided on a part of the wire located in the solution 12, so that only the exposed portions function as the cathode and anode 18/20. Similarly, cathode member 18 and anode member 20 may each be electrically connected to an separate electrical conductor electrically connecting the cathode and anode, respectively, to a power source. Upon passage of current through the lead wires from a 1.5 volt battery by wire leads sealed inside the device and coming into contact with the solution of oxidant generating formulation sealed inside the insert, nascent iodine is electrolytically generated within the chamber 14 of the insert member 10. The elemental iodine diffuses laterally (arrows projecting outward planar to the long axis of the device) across the silicone casing, conferring to the implant site anti-infective activity. An insulator sleeve 26 separates the lead wires. Although both the anode member and the cathode member are illustrated within the solution 12 containing the oxidant generating formulation, one of skill in the art will recognize that one of the cathode and anode (depending on the nature of the oxidant generating formulation) may be outside of the solution 12 so long as electrical current is able to pass between the cathode and anode. FIG. 4A illustrates a transverse cross sectional view of the insert shown in FIG. 4, taken along line 4A–4A. Although the embodiment illustrated in FIG. 4A, and the illustrated embodiments discussed below, has a circular transverse cross section, the device of the invention may have a variety of suitable configurations including oval, and angular, such as rectangular and triangular, shaped cross sections.

In the case of the insert designed for loading free elemental iodine into an indwelling catheter, or lumenal implant device, the insert may be constructed as a solid, hydrophobic, flexible rod, fabricated to the length and diameter of the lumen device in which it is to be inserted. The rod can be fabricated with longitudinal grooves running along its axis to allow fluid to flow past the lumen insert, or drain from the insert, with the rod in place during transfer of iodine to the walls of the implant device. It can be fabricated to serve as a plug, fitting snugly against the inner walls of the lumenal wall of the implant device during transfer of iodine to the implant device requiring treatment.

The insert addresses transfer of anti-infective iodine activity to lumenal walls of implant devices such as venous or arterial catheters, or drain tubes, where direct injection of fluid formulations into a body fluid is unacceptable because of pH incompatibilities, the possibility of adverse reactions of components of the iodine generating formulation with constituents in blood, or the possibility of thrombolytic reactions induced with delivery of fluid directly into the blood stream.

As a solid rod, it serves as a solid-phase transporter of free iodine. In the case of a venous catheter, for example, the rod would displace blood from the catheter, yet upon removal, leave no residual fluid within the lumen space. Suitable materials for fabrication of a rod insert include, but are not restricted to, hydrophobic polymers such as polyethylene, Teflon, silicone, polystyrene, polypropylene, polyurethane, and/or polycarbonate. The critical feature is that free iodine formed electrolytically in the rod insert is able to equilibrate and diffluse out of the rod and into the walls of the implant device whence anti-infective activity is conferred to the implant device.

While it should be appreciated that there is latitude in the design of an insert, preferably the insert should slide smoothly through the lumen of the implant device without binding or grabbing too tightly against the walls of the implant to be treated precluding its easy positioning within the lumen. This dictates that it have sufficient stiffness, yet flexibility, so that it can be pushed into the lumen without hanging up on the walls of the lumen. In a practical application, the insert should occupy not less than about 5% nor more than about 90% of the total volume of the lumen space when inserted, with the preferred diameter approximately 80% of the inner lumenal wall diameter of the implant device. Furthermore, in a preferred embodiment, the ends of the rod should be rounded so as to allow it to slide freely along the inner lumenal wall of the implant without binding or catching. In the case of a plug design, the plug can be designed to fit snugly into the lumen space to preclude leakage of fluid within the lumen to the exterior of the implant device.

It is desirable that the reservoir for holding free iodine is also of practical volume so as to allow for a significant transfer of iodine to the walls of the implant device conferred with anti-infective activity. Levels of nascent iodine transferred to the treatment site should be not less than 2 ppm nor more than about 300 ppm, preferably about 5 ppm.

An alternative insert member which embodies features of the invention, has the anode member embedded within a polymeric wall of the insert member. The polymeric wall, formed of a polymeric material such as silicone, is impregnated with the oxidant generating formulation, such as potassium iodide. In such embodiment, the insert member is a solid-walled member, however, in alternative embodiments, the insert member may be hollow, so that the polymeric wall having the oxidant generating formulation dispersed therein defines at least in part a lumen or chamber. The cathode member is also included in fabrication of the device running parallel to the anodic lead wire. Arrows lateral to the long axis of the device illustrate the egress of nascent iodine from the polymer base as it is formed and diffuses outward from the polymeric wall and into surrounding body fluids and tissues in contact with the device.

In the embodiment in which the device is a medical device, such a catheter, the cathode and anode members are similarly provided either within a chamber in the medical device having a solution of the oxidant generating formulation therein, or within a polymeric wall of the medical device. FIG. 6 illustrates a Foley type catheter 40 having a shaft 41, having a proximal end 42, a distal end 43, a balloon 44 on a distal section of the shaft, and an inflation lumen 45 in fluid communication with the balloon 44 and a port 47 in the proximal end of the device. A drainage lumen 46 (FIG. 6A) extends from a proximal port 48 to a port in the distal end of the catheter. In the embodiment illustrated in FIG. 6, the polymeric wall 50 forming the shaft 41 has oxidant generating formulation 52 impregnated therein. As discussed above in relation to the embodiment, cathode and anode members 18/20 are embedded in the polymeric wall 50. A connector 49 provides electrical connection between a power source such as a battery (not shown) and the cathode and anode members 18/20. Although not illustrated, in one embodiment, a medical device such as catheter 40 illustrated in FIG. 6, is provided with a chamber in at least a section thereof, having a solution of the oxidant generating formulation in the chamber along with the cathode and anode members. The chamber may be similar to the inflation lumen 45 illustrated in FIG. 6, except the chamber has closed proximal and distal ends.

Formulations Required for Electrolytic Generation of Nascent Iodine and Construction of the Anti-infective Generating Device The chemical reactions involved for electrolytic generation of nascent iodine are illustrated in equations (1) and (2) using inorganic iodide, and the iodate oxide salt of iodine, respectively.

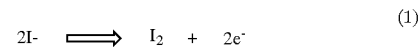

$$2I^- \rightleftharpoons I_2 + 2e^- \quad (1)$$

$$10e^- + 2IO_3^- + 12H^+ \rightleftharpoons I_2 + 6H_2O \quad (2)$$

In equation (1), the oxidation of inorganic iodide is depicted occurring at the anodic lead where electrons are given up to the electrode concomitant with reduction of an electron acceptor at the cathodic lead. In equation (2) the reduction of iodate is depicted occurring at the cathodic lead where electrons given up by the cathode to iodate serve to reduce iodate to a lower oxidation state illustrated here by formation of nascent iodine. The latter reaction is complex, however, because the stoichiometry of the redox reaction also requires a source of protons in driving formation of nascent iodine. Furthermore, it can be appreciated by those familiar with the chemical art that iodide, also formed by reduction of iodate, in the presence of excess iodate and protons, can be converted to nascent iodine as illustrated in equation (3).

$$5I^- + IO_3^- + 6H^+ \rightleftharpoons 3I_2 + 3H_2O \tag{3}$$

Certain metal ions that can react with iodide, and catalyze its oxidation to iodine, are also of importance in this regard. For example, Cupric (II) or iron (III) ions, formed in solutions with electrolytic currents passing through wire leads fabricated from copper or iron, respectively, can further oxidize iodide to nascent iodine. Copper (II) reacts in solution with iodide to form cupric iodide that is known by those knowledgeable in the art to then convert to cuprous iodide and iodine. Similarly, ferric ion is capable of oxidizing inorganic iodide to iodine concomitant with its reduction to the ferrous ion. In the solvated form, both metals also catalyze Fenton type free radical reactions, and they form complex insoluble precipitates, especially at neutral or slightly alkaline pH. Hence, while the chemistry of nascent iodine production generated electrolytically, especially using oxide salts of iodine, is complex, certain features stand out. First, the rate of nascent iodine formation is markedly enhanced under acid conditions. Second, depending upon the presence or absence of specific metal ions, for example, the rate of nascent iodine generation may be enhanced through secondary metal oxidation reactions.

By contrast, nascent iodine formation generated electrolytically using inorganic iodide is independent of pH so far as oxidation of iodide is concerned. However, because of the insolubility of heavy metal halides, especially at neutral or more alkaline pH conditions, and the tendency of heavy metals to form insoluble hydroxide complexes at neutral or alkaline pH, ionization and solubilization of heavy metals in the electrolytic precursor reservoir containing inorganic iodide is undesirable. The latter precipitation reactions interfere with formation of nascent iodine, possibly because of sequestration of iodide in precipitated complexes.

In a preferred embodiment of the invention, inorganic iodide made up in water to a concentration ranging from 0.1 to 200 mM, preferably about 100 mM, is contained within an inner precursor reservoir of the implant device. Inert electrical cathodic and anodic wire leads made of platinum, or other noncorrosive electrical conductor designed so as to not release heavy metals into the reservoir solution, are also placed in parallel inside the precursor reservoir, communicating to an electrical power source such as a 1.5 volt battery (cf., FIG. 4).

Alternatively, the precursor reservoir may be filled with sodium iodate solution ranging from about 1 mM to 30 mM, preferably about 15 mM, and also containing a pH donor capable of maintaining the pH in the range of from about 2.0 to 5.0, preferably about 2.5. The pH donor may be a formulated from an organic acid such as citric acid, acetic acid, an anhydride such as iodine pentoxide, or other suitable proton donor capable of maintaining a low pH in allowing for nascent iodine formation to occur upon reduction of the oxide salt of iodine in accordance with the reaction outlined in equation (2). A preferable pH donor should be made up in a concentration range of from about 0.1 to 100 mM, preferably about 25 mM. Citric acid is a preferable proton donor made up to a final concentration in the reservoir of 25 mM. In the case of the wire leads, the cathodic and anodic wire leads may be made up of an inert metal such as platinum, or nickel coated copper, copper, iron or gold, although the preferred wire lead is platinum that resists corrosion. However, a variety of suitable materials may be used to form the anode and cathode members, including carbon and aqueous salt bridges.

Other noncorrosive wire leads, including nonmetallic conductors may, in principle, be substituted in place of the above, as the invention is dependent upon electrolytic oxidation and reduction processes between inorganic iodide, or oxides of iodine, and the conductor, respectively, and thus barring adverse reactions of the conductor with precursor substrates of nascent iodine the nature of the conducting element is not critical. The electrical conducting leads need to make contact with the precursor solution, and they must be powered by a low current generating device, such as a 1.5 volt battery (cf., FIG. 4), or other suitable current generator.

As an implant insert, or in conferring the capability of generating anti-infective activity to a medical device to be fabricated into a specific form for a particular medical application, the precursor reservoir of inorganic iodide and lead wires may also be incorporated directly into the polymer base used to fabricate the device. In this embodiment, finely ground inorganic iodide (<200 micron particle size) is uniformly dispersed as a dry powder directly into the polymer base prior to curing of the polymer. The solid salt is ground to a fine powder, and mechanically mixed into the polymer. Lead wires are incorporated into the polymer base just prior to curing, or extruded along with the polymer from mandrels used in the fabrication of the device. The cathodic and anodic wires designed for carrying current into the precursor reservoir from whence nascent iodine is formed are positioned in parallel to one another from about 0.01 to about 1 cm apart, depending upon the physical dimensions of the device, but in a manner so that they do not physically come into direct contact with one another. Suitable hydrophobic elastomers include polyurea, polyurethane, ethylene vinyl acetate, polyvinylchloride, polyesters, polyamides, polycarbonate, polyethylene, polymethyl methacrylate, cellulose esters such as ethyl, methyl and propyl forms, polypropylene, polystyrene, polytetrafluoroethylene, poly (ethylenevinyl acetate), elastomeric organosilicon polymers, poly(hydroxyl alkyl esters), copolymers and thermoplastic hydrophobic combinations thereof, wherein the dry iodine-generating component is an iodine salt selected from the group consisting of anhydrous alkali iodine salts such as potassium or sodium iodide at a concentration of from about 0.01% to about 16%, preferably about 8% (by weight).

A critical factor in the fabrication and operation of the invention is that the fabricated polymer must be able to conduct a current between the cathodic and anodic lead wires allowing for nascent iodine formation to ensue. The amount of current passing between the cathodic and anodic lead wires can vary from a few microamperes to a high of about 500 milliamperes depending upon the chemical properties of the polymer base, the concentration of iodide salt mixed into the polymer, and the water content of the precursor reservoir.

SPECIFIC EXAMPLES RELEVANT TO THE INVENTION

Example 1

Dependence of Rate of Electrolytically Generated Nascent Iodine Versus Composition of the Metal Wire Lead Submerged in Iodide and Iodate Precursor Reservoirs.

FIG. 1 compares the rates of nascent iodine formation upon passing current supplied by a 1.5 volt battery through 24 gauge cathodic and anodic wire leads of varying metal compositions, as indicated, for five minutes at room temperature in solutions made up at 100 mM potassium iodide in distilled water (filled bars), and corresponding rates with submersion of the leads in stock solutions made up at 126 mM sodium iodate, 25 mM citric acid, pH 2.4. The wire leads were formed of pure platinum (Pt), nickel coated copper (Ni—Cu), copper (Cu), iron (Fe) and silver (Ag). Lead wires were placed approximately 0.5 cm apart from one another in parallel in a total volume of 5 ml precursor reservoir solution. The physical dimensions of the glass reservoir in which the lead wires were placed corresponded to approximately 1 ml precursor solution bathing each centimeter of wire lead. Nascent iodine was allowed to form at the corresponding cathode, or anode, depending upon the composition of the solution under static conditions (e.g., without mixing solutions during the five minute interval in which iodine was allowed to form). The concentration of nascent iodine formed was determined by extraction of the test solutions into an equal volume of chloroform, and then measuring iodine recovered in the chloroform extract at 520 nm using an absorptivity coefficient for conversion of recovered iodine in ppm (parts per million) of 0.333 ppm/milliabsorbance-cm. In iodide solutions, nascent iodine was observed to form at the anode. In the iodate/citric acid solutions, iodine formed at the cathode.

FIG. 1 shows that nascent iodine was formed in all of the lead wire samples tested, but most preferably in lead wires made of platinum in precursor reservoir solutions made up with inorganic iodide, and most preferably in lead wires made of copper in precursor reservoir solutions made up with iodate/citric acid, respectively. Large quantities of nascent iodine were generated under the above conditions at levels sufficient to kill micro-organisms (e.g., >2 ppm). Nascent iodine achieved a concentration in excess of 20 ppm with platinum wire leads upon passing current through the wires for a period of five minutes in the iodide precursor reservoir test solution. In iodate/citric acid precursor reservoir test solutions, copper lead wires yielded nascent iodine concentrations in excess of 40 ppm per five minute interval of electrolysis. In the absence of current, iodine formation was not detected in any of the test wire leads evaluated.

Example 2

Dependence of Rate of Electrolytically Generated Nascent Iodine with Copper Metal Wire Leads Submerged in Iodide and Iodate Precursor Reservoirs versus pH of the Reservoir Solution.

Figure 2:
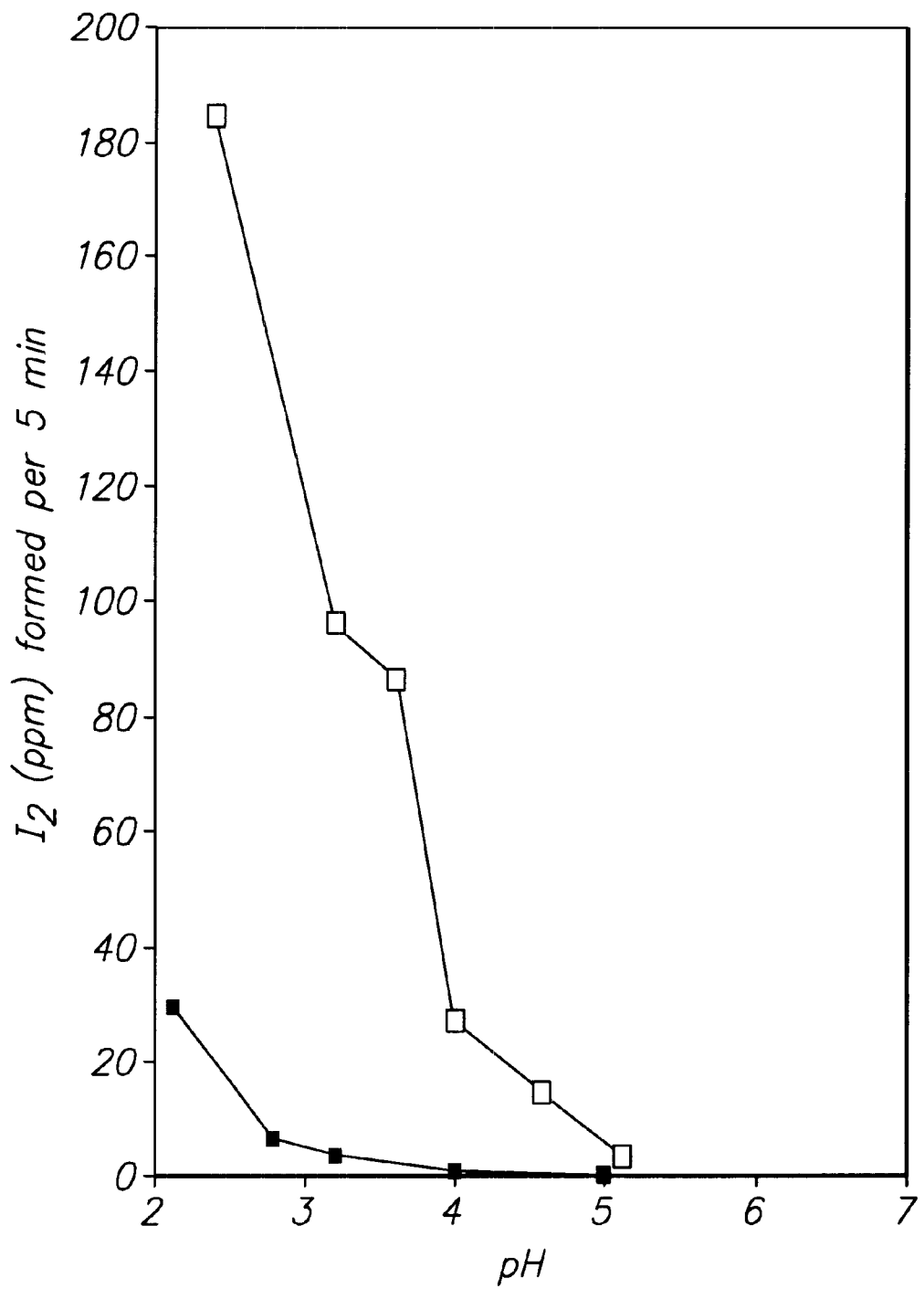
FIG. 2 shows the pH dependence of nascent iodine generation formed electrolytically upon immersion of copper cathodic and anodic lead wires into 3 ml solutions made up at varying pH values as indicated, and containing sodium iodate (open symbols) versus potassium iodide (closed symbols).

FIG. 2 summarizes test results in examining the pH dependency of nascent iodine formation formed electrolytically upon passing current from a 1.5 volt battery through 24 gauge wire leads submerged in 50 mM potassium iodide (closed symbols) and 50 mM sodium iodate (open symbols) precursor reservoir solutions also containing 50 mM potassium citrate adjusted to various pH values as indicated. The cathodic and anodic copper wire leads were wrapped in parallel around a thin polyethylene strip (approx. 1 mm thick by 5 mm in width and 50 mm in length), and spaced approximately 2 mm apart from one another, and the entire apparatus submerged in precursor reservoir test solutions at the varying pH values indicated, and then connected to a 1.5 volt battery for five minutes. Nascent iodine formed in the iodate/citrate buffer precursor reservoir test solution was quantitated as in Example 1. Nascent iodine formed in the iodide/citrate buffer precursor reservoir test solution was quantitated by measuring the rate of tri-iodide formed in five minutes by tracking absorbance changes at 350 nm spectrally and comparing the absorbances against standard calibration curve constructed with crystalline elemental iodine made up in potassium iodide as the tri-iodide complex. Lead wires were submerged at approximately 3 cm length segments per ml precursor reservoir test solution.

As in FIG. 1, copper wire leads produce nascent iodine most robustly when submerged in iodate/citric acid solutions as opposed to iodide, achieving rates of nascent iodine in excess of 180 ppm per five minutes of current flow near pH 2.5, and falling precipitously to very low levels as the pH exceeds approximately 5.0. The low pH dependency affirms the requirement of protons in driving formation of nascent iodine in accordance with equations C2) and (3) (see above, Formulations Required for Electrolytic Generation of Nascent Iodine and Construction of the Anti-infective Generating Device). Nascent iodine formation was also enhanced electrolytically in precursor reservoir solutions made up in iodide and citric acid as the solutions were made more acidic. This latter phenomenon reflects the propensity of inorganic iodide to oxidize more readily, in general, at low pH, even in the absence of current. However, unlike inorganic iodide, iodate in the presence of excess protons in the pH range from about 2.0 and above showed no tendency to form free iodine except upon application of current to the lead wires. As expected, iodine was observed to form at the cathode in iodate/citrate buffered precursor reservoir test solutions, and at the anode in iodide/citrate buffered precursor reservoir test solutions, respectively.

Example 3

Dependence of Rate of Electrolytically Generated Nascent Iodine with Copper Metal Wire Leads Submerged in Iodate Precursor Reservoir at Fixed pH versus Available Iodate Concentration.

Figure 3:
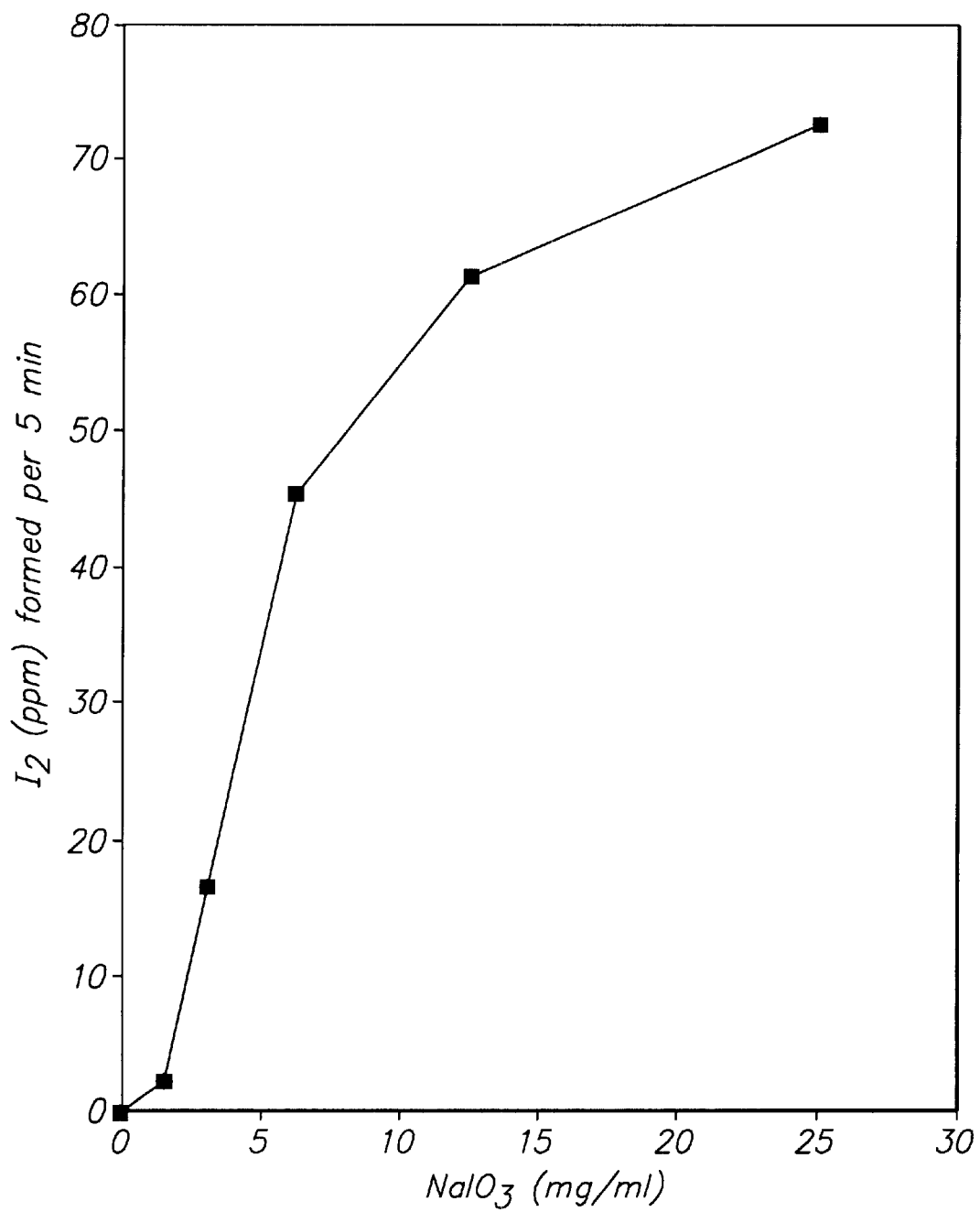
FIG. 3 shows the dependency of the rate of electrolytically generated nascent iodine formation on sodium iodate concentration upon submersion of copper cathodic and anodic lead wires into prepared solutions, and application of current to the lead wires using a 1.5 volt battery.

FIG. 3 shows that the rate of nascent iodine generated electrolytically using 24 gauge copper wire leads submerged in 50 mM potassium citrate buffer, pH 3.6, also made up at varying concentrations of sodium iodate, rises sharply in proportion to the iodate concentration presented to the lead wires. Wire leads were submerged in test precursor reservoir solutions at approximately one ml per cm wire lead, and nascent iodine formed quantitated a in example 1. From about 0.1% to about 0.7% sodium iodate, the rate of nascent iodine formation seen with application of current from a 1.5 volt battery rose linearly, approaching approximately 45 ppm per five minutes of current flow at 0.7% sodium iodate. The rate of nascent iodine formation appeared to slow down thereafter with further increases in sodium iodate concentration, achieving a rate of about 70 ppm per five minutes electrolysis at a final concentration of sodium iodate in the precursor reservoir solution of approximately 2.5%. No iodine was formed in the absence of current flow at any of the concentrations examined.

Example 4

Fabrication of an Electrolytic Nascent Iodine Generator Encased in a Silicone Tube and Egress of Nascent Iodine Formed Electrolytically Across the Silicone Casing Wall and into Solution Bathing the Walls of the Iodine Generating Device.

To verify the efficacy of moving nascent iodine across the walls of a silicone casing containing precursor reservoir solutions and lead wires designed for electrolytic generation of iodine, devices were fabricated as illustrated in FIG. 4, and immersed in 10 mM potassium iodide made up in distilled water to trap iodine egressing across the walls of the iodine generating devices. Silicone tubing approximately 10.5 cm in length with approximately 1 mm thick walls and an internal diameter of approximately 3 mm, was filled with approximately 0.2 ml of precursor reservoir test solutions and wire leads insulated from one another by a polyethylene sleeve, and running parallel to one another the length of the device, were submerged into the inner reservoir containing precursor reservoir solutions (cf., FIG. 4 and Table 1). The bottom end of each casing was capped tightly with a glass plug to form a leak-proof inner reservoir. The iodine generating devices were then rinsed thoroughly on their outer sides and placed in 10 ml of 10 mM potassium iodide in a manner so that the upper sections could not leak into the potassium iodide solution bathing the exterior walls of the devices. Current was then applied for 90 minutes by connecting the cathodic and anodic lead wires to a 1.5 volt battery to allow iodine to form within the inner precursor reservoirs, and to allow for its diffusion laterally to the exterior potassium iodide solution bathing the devices. Following 90 minutes of current flow, the iodine generating devices were carefully removed from the iodide solutions, and nascent iodine recovered in the external solutions quantitated spectrally at 350 nm as in Example 2.

TABLE 1

Recovery of Nascent Iodine Formed Electrolytically and Transported Across the Walls of a Silicone-Encased Iodine Generating Device[a]

| Composition of Wire Lead | Sodium Iodate/Citric Acid[b] (ppm per 90 min current flow) | Potassium Iodide[c] (ppm per 90 min current flow) |
|---|---|---|
| iron | 27 | 0 |
| Copper | 3.5 | 0 |
| platinum | 4.5 | 2.7 |

[a]Recovered in 10 ml 10 mM potassium iodide bathing iodine generating devices.
[b]Precursor reservoir solution - 126 mM sodium iodate, 25 mM citric acid, pH 2.4.
[c]Precursor reservoir solution - 100 mM potassium iodide made up in distilled water.

Table 1 summarizes results showing that nascent iodine at levels above 2 ppm were easily recovered in the external bathing solutions in each case in the iodate/citric acid precursor reservoir iodine generating devices whether the lead wires were made of iron, copper or platinum. The higher yield with iron wire leads appears to be linked with release of ferric ions into the precursor solution upon application of current to the lead wires immersed in the inner reservoir, and secondary oxidative reactions thereafter driving formation of nascent iodine which enhanced the yield of recovered iodine in the external potassium iodide solutions bathing the devices. Dye (toluidine blue) confirmed that the method of capping the ends of the silicone tubes was effective in producing a leak-proof compartment. With potassium iodide added to the inner precursor reservoir of the iodine generating devices, only platinum lead wires appeared effective in generating iodine at levels sufficient to egress across the silicone wall casing into the external potassium iodide solution (cf., Table 1).

The results summarized in Table 1 affirm that nascent iodine can be generated electrolytically within an insert device fabricated in a manner excluding direct contact between the electrodes, precursor reservoir iodine generating solution, and external medium whence anti-infective activity in the form of nascent iodine is to be transferred. While the top of the casing was left open and accessible in the example cited above, it can be appreciated by those familiar with the art of constructing silicone and other polymer rod devices of this type that sealing of the upper chamber so that the device may be inverted, or rotated, without spillage of its content, poses no significant barrier those knowledgeable in the art of extrusion and molding of sealed polymer devices. Various shapes similarly may be constructed from the example cited to fit as inserts in lumenal medical devices, or as plugs, wherein the shape is dictated by the specific device to be fitted without sacrificing the fundamental principles for generating nascent iodine electrolytically as outlined in the above example.

Example 5

Dependence of the Rate of Electrolytically Generated Nascent Iodine with Platinum Metal Wire Leads Submerged in Iodide versus Iodide Concentration.

Figure 5:
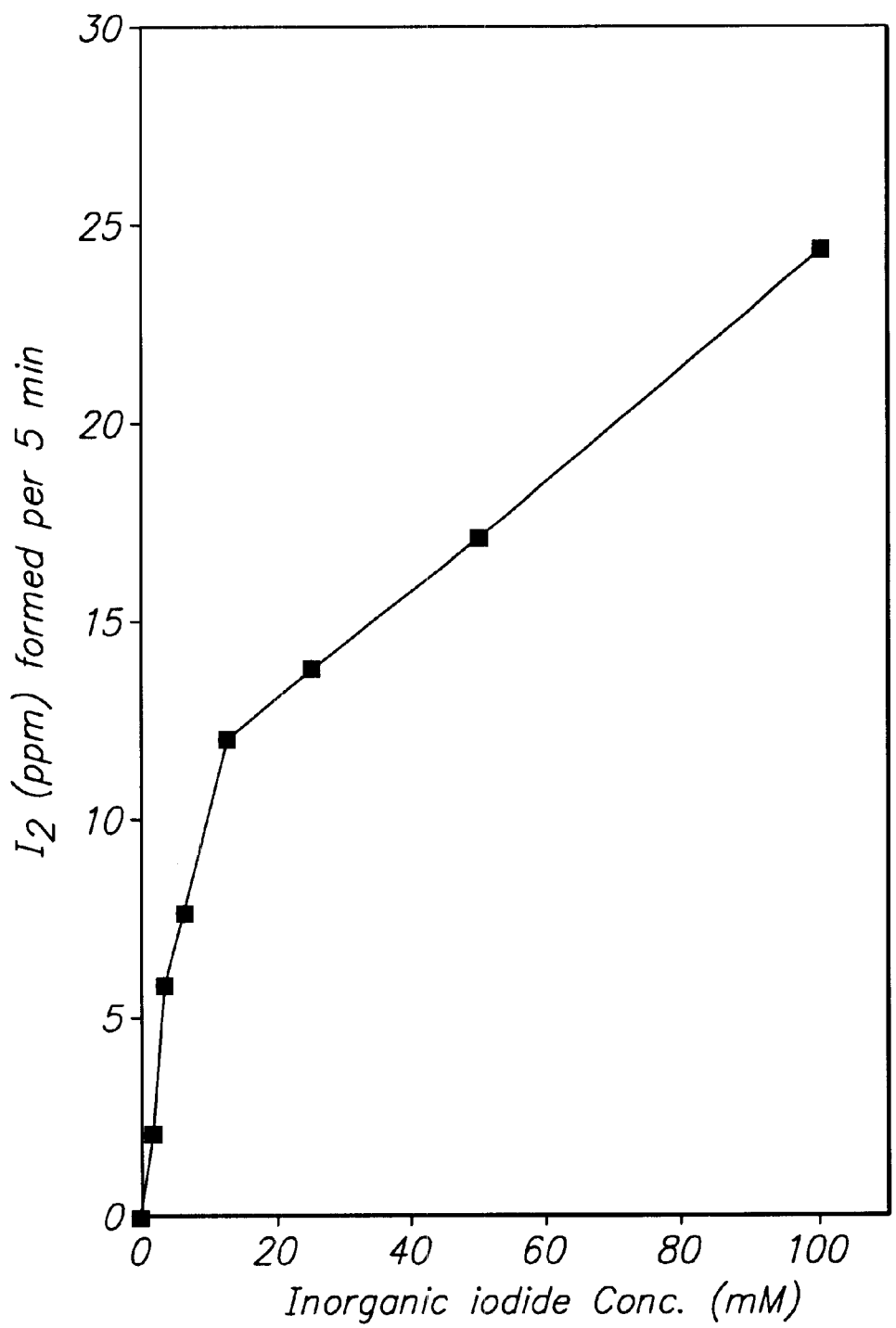
FIG. 5 shows the dependency of the rate of electrolytically generated nascent iodine formation on potassium iodide concentration at neutral pH upon submersion of platinum cathodic and anodic lead wires into test solutions, and application of current to the lead wires using a 1.5 volt battery.

FIG. 5 shows the dependence of nascent iodine formation generated by electrolysis using 24 gauge platinum wire leads submerged in precursor reservoir solutions of potassium iodide made up as indicated in distilled water. The physical dimensions of the reservoir in which the lead wires were placed corresponded to approximately 1 ml precursor solution bathing each centimeter of wire lead. The cathodic and anodic wire leads were connected to a 1.5 volt battery for five minutes at room temperature. Nascent iodine generated was quantitated by spectroscopic analysis of the test solution at 350 nm as the tri-iodide complex as in Example 2.

Electrolytic generation of nascent iodine using iodide as the precursor and platinum electrodes proved extremely efficient as evident from the data shown in FIG. 2. Nascent iodine was formed at a concentration sufficient to confer to the solution anti-infective activity (e.g., >2 ppm) at concentrations of iodide in the precursor reservoir as low as 2 mM (e.g., ~0.03%).

The response curve regarding the rate of nascent iodine formation versus iodide concentration in the precursor reservoir appeared biphasic, showing a sharp linear rise in nascent iodine production up to about 8 mM potassium iodide, and then a second lesser linear rise which had not yet peaked even at the highest concentration of potassium iodide tested (100 mM). At 100 mM potassium iodide the rate of nascent iodine formation at nearly 25 ppm was more than 10-fold the concentration necessary to confer to solutions anti-infective activity. Hence, as shown here, iodide alone in the precursor reservoir can by electrolysis serve as an efficient method of generating nascent iodine in conferring anti-infective properties to fluids.

Example 6

Fabrication of a Silicone Insert with the Capability of Forming Nascent Iodine Electrolytically.

This example illustrates an elongated silicone insert designed for its capability of generating nascent iodine, and conferring to solutions in which it comes into contact anti-infective activity. This insert was prepared by grinding solid potassium iodide to a fine powder of less than 200 microns with passage of the ground salt through a stainless steel mesh screen, and then mixing the dry ground salt in equal parts of NuSil Technology elastomer Part A #4940 (Pt catalyzed—polydimethylvinyl siloxane) and Part B #4940 (polymethylhydride siloxane) to a final concentration of 8% solid by weight relative to the silicone elastomers. Platinum wire leads (24 gauge) were then embedded in the elastomer mixture containing potassium iodide in parallel to one another spaced approximately 1 mm apart, and spanning a longitudinal distance of approximately 8 cm, yielding a cylindrically coated set of leads with the cathodic lead wire buried centrally within the polymer base. The silicone elastomer, impregnated with potassium iodide, and containing the wire inserts, was then cured at 160° C. for 8 minutes and soaked overnight in distilled water to rehydrate the polymer base. Thereafter the insert was submerged in 6 ml of mM potassium phosphate buffer, 0.9% sodium chloride, pH 7.4, and the protruding wire leads connected to a 1.5 volt battery. Current was applied to the insert through the wire leads embedded in the polymer for a period of 90 minutes at room temperature. During this time the silicone insert took on a faint yellow and pink-violet coloration indicative of nascent iodine formation. At the end of the 90 minute interval, the silicone insert device was removed, and the phosphate buffer made up in isotonic saline was extracted in chloroform from which the concentration of nascent iodine was determined by spectroscopy at 520 nm as in Example 2. The external solution in contact with the silicone insert showed a concentration of nascent iodine of 6 ppm.

Similar results were obtained at varying other iodide compositions taken up in the silicone elastomer consistent with the dose dependency of nascent iodine formation on availability of iodide as indicated in Example 5. Silicone inserts left to soak in phosphate-saline solutions without application of a current through the lead wires produced no detectable iodine.

While the invention has been described in terms of certain preferred embodiment, those of skill in the art will recognize that certain modifications can be made without departing from the scope thereof. Moreover, although individual features of the embodiments may be shown and described in some of the embodiments and not others, those skilled in the art will recognize that individual features of one embodiment can be combined with any or all features of the other embodiments.

REFERENCES

U.S. Patents:

U.S. Pat. No. 4,278,548 Bettinger et al. (1981) Control of biological growth in reverse osmosis permeators.

U.S. Pat. No. 4,312,833 Clough et al. (1982) Sterilizing hydrophilic contact lenses.

U.S. Pat. No. 4,476,108 Kessler et al. (1984) Bactericidal method.

U.S. Pat. No. 5,156,164 LeVeen and LeVeen (1992) Iodine contraceptive sponge.

U.S. Pat. No. 5,232,914 Fellman (1993) Solid, storage-stable, germicidal. Pre-iodine composition.

U.S. Pat. No. 5,230,783 Socrtichini et al. (1993) Electrolytic cell and process for the labeling of proteins and peptides.

U.S. Pat. No. 5,246,561 Scortichini et al. (1993) Electrolytic cell and process for the labeling of proteins and peptides.

U.S. Pat. No. 5,607,681 Galley et al. (1997) Antimicrobial compositions.

U.S. Pat. No. 5,648,075 Kessler et al. (1997) Iodine based germicidal composition.

U.S. Pat. No. 5,695,458 Shikani and Domb (1997) Anti-infective polymer-iodine coating for blood collection and delivery systems.

U.S. Pat. No. 5,762,638 Shikani and Domb (1998) Anti-infective and anti-inflammatory releasing systems for medical devices.

U.S. Pat. No. 5,849,241 Kessler (1998) Ophthalmic non-irritating iodine medicament.

Other Relevant Articles:

Barabas, E. S. and Brittain, H. G. (1998). Povidone-Iodine in Analytical Profiles of Drug Substances and Excipients (ed., Brittain, H. G.) Vol. 25, AP, San Diego, pp. 341–462.

Birnbaum, L. M., Hopp, D. D. and Mertens, B. F. (1982) The Role of Iodine-Releasing Silicone Implants in Prevention of Spherical Contractures in Mice. Plastic & Reconstructive Surgery 69 (6): 956–959.

Caufield, P. W. and Wannemuehler, Y. M. (1982) In vitro susceptibility of streptococcus mutans 6715 to iodine and sodium fluoride, single and in combination, at various pH values. Antimicrob. Agents Chemother. 22 (1): 115–9.

Gordon, J. (1993) Opening address, Closing remarks, and articles therein—Second Asian Pacific Congress on Antisepsis (Hong Kong) in Postgrad Med J 69 (suppl. 3), S1–S134.

Gristina, A. G. (1981) Biomaterial-Centered Infection: Microbial Adhesion Versus Tissue Integration. Science 237: 1588–1595.

Gupta, K., Scholes, D. and Stamm, W. E. (1999) Increasing Prevalence of Antimicrobial Resistance Among Uropathogens Causing Acute Uncomplicated Cystitis in Women. JAMA 281 (8): 736–738.

Houang, E. T., Gilmore, O. J., Reid, C. and Shaw, E. J. (1976) Absence of bacterial resistance to povidone iodine. J. Clin. PathoL 29 (8): 752–5.

Jansen, B. et al. (1992) In-vitro efficacy of a central venous catheter complexed with iodine to prevent bacterial colonization. J. Anfimicrobial Chemotherapy 30: 135–139.

Kristinsson, K. G. et al. (1991) Antimicrobial activity of polymers coated with iodine-complexed polyvinylpyrrolidone. J. Biomaterials Applications 5: 173–184.

Krohn, K., Sherman, L. and Welch, M. (1972) Studies of radioiodinated fibrinogen. I. Physicochemical properties of the ICl, chloramine-T, and electrolytic reaction products. Biochim. Biophys. Acta 28: 404–13.

LeVeen, H. H. et al. (1993) The mythology of povidone-iodine and the development of self-sterilizing plastics. Gynecology & Obstetrics 176: 183–190.

MacLellan, D. G. (1997) Foreword; Ermini, M. (1997) Current Povidone-Iodine Research: A Summary of the Papers Presented; see also articles therein—Third Asian Pacific Congress on Antisepsis (Sidney) in Dermatology 195 (suppl. 2), S1–S120 (and abstracts S121–S159).

Malan, P. G. et al. (1974) Proceedings: an electrolytic procedure for iodination of glycoprotein and protein hormones. J. Endocrinol. 61 (2): XLII.

Massaglia, A. et al. (1969) Iodination of insulin in aqueous and organic solvents. Biochem. J. 115:11–18.

Morain, W. D. and Vistnes, L. M. (1977) Iodinated silicone—an antibacterial alloplastic material. Plastic & Reconstructive Surgery 59 (2): 216–22.

Nielsen, S. T. et al. (1979) The electrolytic preparation of bioactive radioiodinated parathyroid hormone of high specific activity. Anal. Biochem. 92 (1): 67–73.

Pennisi, F. and Rosa, U. (1969) Preparation of radioiodinated insulin by constant current electrolysis. J. Nucl. Biol. Med. 13 (1): 64–70.

Raad, I. et al. (1996) In vitro antimicrobial efficacy of silver iontophoretic catheter. Biomaterials 17 (11): 1055–9.

Scarpace, P. J. and Deftos, L. J. (1977) Preparation and immunological characteristics of biologically active radioiodinated human calcitonin. Endocrinology 101 (5): 1398–405.

Shikani, A. H. et al. (1996) Polymer-iodine inactivation of the human immunodeficiency virus. J. Amer. College of Surgeons 183: 195–200.

Teulings, F. A. G., and Biggs, G. J. (1970) Study of electrolytic labeling of fibrinogen with 131-iodine by sephadex G-10 gel filtration. Clin. Chim. Acta 27: 57–64.

Tyagi, M. and Singh, H. (1997) Preparation and antibacterial evaluation of urinary balloon catheter. Biomedical Sciences Instrumentation 33: 240–45.

Zhang, X., Whitboume, R. and Richmond, R. D. (1997) Antiinfective coatings for indwelling medical devices. Medical Plastics and Biomaterials, November/December Issue, pp. 16–24.

What is claimed is:

1. An anti-infective device for insertion within a lumen of, emplacement around, or for construction within, an implantable medical device to confer to the medical device sustained anti-infective properties to prevent bacterial growth and propagation on the medical device when implanted, comprising
    a) an oxidant generating formulation contained within at least a section of the anti-infective device; and
    b) at least one of a cathode member and an anode member in the section of the anti-infective device, configured to electrolyze the oxidant generating formulation to electrolytically generate an anti-infective oxidant.

2. The anti-infective device of claim 1 wherein the oxidant generating formulation comprises a solid dispersed in a polymeric wall of the anti-infective device, and wherein the cathode and anode members are embedded within the polymeric wall of the anti-infective device.

3. The anti-infective device of claim 1 wherein the oxidant generating formulation comprises a solution contained within a chamber in the anti-infective device, and wherein the cathode and anode members are located within the chamber in contact with the solution.

4. The anti-infective device of claim 1 wherein the medical device comprises a catheter.

5. The anti-infective device of claim 1 wherein the anti-infective device comprises an insert member configured to be slidably insertable into a lumen of a medical device or around the medical device, to transfer the anti-infective oxidant from the anti-infective device into a wall of the medical device.

6. The anti-infective device of claim 1 including a power source electrically connected to the cathode and anode members.

7. The anti-infective device of claim 1 wherein the anti-infective oxidant is elemental iodine, and about 5 ppm to about 100 ppm elemental iodine is generated.

8. The anti-infective device of claim 1 wherein the oxidant generating formulation comprises an iodide, and wherein the anti-infective oxidant is elemental iodine.

9. The anti-infective device of claim 8 wherein the anti-infective device is a polymeric cylindrical member having the oxidant generating formulation dispersed within at least a portion of a wall of the device.

10. The anti-infective device of claim 9 wherein the iodide is selected from the group consisting of potassium iodide and sodium iodide, and the concentration of the iodide in the at least a portion of the device is about 0.01% to about 16% by weight.

11. The anti-infective device of claim 9 wherein the polymeric cylindrical member is solid-walled, and wherein the anode member is located substantially centrally within the portion of the anti-infective device.

12. The anti-infective device of claim 8 wherein the anti-infective device has a chamber therein containing a solution of the oxidant generating formulation therein.

13. The anti-infective device of claim 12 wherein the anode member is located substantially centrally within the chamber in contact with the solution.

14. The anti-infective device of claim 12 wherein the iodide is selected from the group consisting of potassium iodide and sodium iodide, and the concentration of the iodide in the solution is about 0.1 to about 200 mM.

15. The anti-infective device of claim 1 wherein the oxidant generating formulation comprises an iodate, and wherein the anti-infective oxidant is elemental iodine.

16. The anti-infective device of claim 15 wherein the anti-infective device is a cylindrical member having the oxidant generating formulation dispersed within at least a portion of a wall of the anti-infective device.

17. The anti-infective device of claim 16 wherein the iodate is selected from the group consisting of potassium iodate and sodium iodate and the concentration of the iodate in the at least a portion of the anti-infective device is about 0.01% to about 16% by weight, and wherein the oxidant generating formulation further comprises a proton donor.

18. The anti-infective device of claim 16 wherein the polymeric cylindrical member is solid-walled, and the cathode member is located substantially centrally within the portion of the anti-infective device.

19. The anti-infective device of claim 15 wherein the anti-infective device has a chamber therein containing a solution of the oxidant generating formulation therein.

20. The anti-infective device of claim 19 wherein the cathode member is located substantially centrally within the chamber in contact with the solution.

21. The anti-infective device of claim 19 wherein the iodate is selected from the group consisting of potassium iodate and sodium iodate, and the concentration of the iodate in the solution is about 1 mM to about 30 mM, and wherein the oxidant generating formulation further comprises a proton donor.

22. The anti-infective device of claim 1 wherein the cathode and anode members comprise wire members formed of a material selected from the group consisting of platinum, nickel coated copper, copper, iron, gold, carbon, and aqueous salt bridges.

23. A method of providing anti-infective activity to an implantable medical device to confer to the medical device sustained anti-infective properties to prevent bacterial growth and propagation on the medical device when implanted, comprising
    a) providing a medical device comprising
        i) an oxidant generating formulation contained in at least a section of the device; and
        ii) at least one of a cathode member and an anode member in the section of the medical device, configured to electrolyze the oxidant generating formulation to electrolytically generate an anti-infective oxidant; and
    b) passing electrical current between the cathode and anode members, to thereby electrolytically generate an anti-infective oxidant.

24. The method of claim 23 wherein (b) comprises electrically connecting the cathode and anode members to a battery to pass about 1 to about 500 microamperes of current between the cathode and anode members.

25. A method of providing anti-infective activity to an implantable medical device to confer to the medical device sustained anti-infective properties to prevent bacterial growth and propagation on the medical device when implanted, comprising
    a) providing a medical device, having a proximal end, a distal end, and a lumen therein
    b) disposing an insert member within the lumen of the medical device or around the medical device, comprising i) an oxidant generating formulation contained in at least a section of the insert member; and ii) at least one of a cathode member and an anode member in the section of the insert member, configured to electrolyze the oxidant generating formulation to electrolytically generate an anti-infective oxidant; and c) passing current between the cathode and anode members, to thereby electrolytically generate an anti-infective oxidant; thereby d) transferring the anti-infective oxidant from the insert member into a wall of the medical device.

\* \* \* \* \*